(12) United States Patent
Pathi et al.

(10) Patent No.: US 8,349,863 B2
(45) Date of Patent: Jan. 8, 2013

(54) CRYSTALLINE POLYMORPHIC FORM OF A CAMPTOTHECIN ANALOGUE

(75) Inventors: Srinivas Laxminarayan Pathi, Karnataka (IN); Shashi Rekha Kanathala, Maharashtra (IN); Manish Gopaldas Gangrade, Maharashtra (IN); Rajendra Narayanrao Kankan, Maharashtra (IN); Dharmaraj Ramachandra Rao, Maharashtra (IN)

(73) Assignee: Cipla Limited, Mumbai (IN)

( * ) Notice: Subject to any disclaimer, the term of this patent is extended or adjusted under 35 U.S.C. 154(b) by 1778 days.

(21) Appl. No.: 11/539,932

(22) Filed: Oct. 10, 2006

(65) Prior Publication Data

US 2007/0105885 A1    May 10, 2007

(30) Foreign Application Priority Data

Oct. 10, 2005  (IN) .................. 1274/MUM/2005

(51) Int. Cl.
  *A61K 31/4745*  (2006.01)
  *C07D 491/22*   (2006.01)
(52) U.S. Cl. .................. 514/283; 546/50
(58) Field of Classification Search .......... 514/283; 546/50
  See application file for complete search history.

(56) References Cited

U.S. PATENT DOCUMENTS

| | | |
|---|---|---|
| 5,004,758 A | 4/1991 | Boehm et al. |
| 5,155,225 A | 10/1992 | Fortunak et al. |
| 5,734,056 A | 3/1998 | Burk et al. |

FOREIGN PATENT DOCUMENTS

| | | |
|---|---|---|
| EP | 1943253 | 7/2008 |
| WO | WO 2005/046608 A2 | 5/2005 |
| WO | 2007042799 A1 | 4/2007 |

OTHER PUBLICATIONS

Boehm et al. "Preparation, testing. . . " CA 112:7778 (1990).*
Dellorco et al. "Preparation of novel crystal . . . " CA 142:487518 (2005).*
Seddon "Psudopolymorph . . . " Crystal growth & design, 4(6)1087 (2004) (two pages from internet).*
Braga et al. "Making crystal . . . " roy. soc. chem. Chem. Commun. p. 3635-3645 (2005).*
Flack "Chiral and achiral crystal structure" Helvettica Chemica Acta v.86, p. 905-921 (2003).*
Zhang et al. "Racemic species of . . . " J. Pharm, Sci. 92(7) p. 1356-1366 (2003).*
Fasel et al. "Amplification of chirality . . . " Nature Jan. 26, (2006) p. 439-452.*
Yokota et al. "Chiral separation . . . " J. chem. eng. Japan 37(10) p. 1284-1285 (2004).*
Berstein "Polymorphism in molecular cyrstals" p. 271-272 (2002).*
Reagent grade methanol, rocky Mountain regent (2010) from internet.*

(Continued)

*Primary Examiner* — Celia Chang
(74) *Attorney, Agent, or Firm* — Conley Rose, P.C.; Rodney B. Carroll

(57) ABSTRACT

The invention relates to a novel crystalline form of topotecan hydrochloride, and methods of making the same. The characteristic XRPD pattern and FT-IT patterns are shown in FIGS. 1 and 2.

19 Claims, 2 Drawing Sheets

OTHER PUBLICATIONS

Foreign communication from a related counterpart application—International Search Report and Written Opinion, PCT/GB2006/003768, Feb. 5, 2007, 10 pages.

Foreign communication from a related counterpart application—International Preliminary Report on Patentability, PCT/GB2006/003768, Apr. 15, 2008, 7 pages.

Chen, M., et al., "Studies on the polymorph of topotecan hydrochloride and its stability," Chinese Journal of Biochemical Pharmaceutics, 2005, vol. 26., No. 5, pp. 279-281.

Vogt, Frederick G., et al., "A study of variable hydration states in topotecan hydrochloride," Journal of Pharmaceutical and Biomedical Analysis, 2006, vol. 40, pages 1080-1088, New York, NY.

* cited by examiner

CRYSTALLINE POLYMORPHIC FORM OF A CAMPTOTHECIN ANALOGUE

CROSS-REFERENCE TO RELATED APPLICATIONS

This application claims priority of Indian Patent Application No. 1274/MUM/2005 filed Oct. 10, 2005 and entitled "Novel Crystalline Polymorphic Form of a Camptothecin Analogue," which application is incorporated by reference herein in its entirety.

FIELD OF THE INVENTION

The present invention relates to a novel crystalline polymorphic form of 10-[(dimethylamino)methyl]-4-ethyl 4,9-dihydroxy-1H-pyrano [3',4':6,7]indolizino[1,2-b]quinoline-3,14(4H,12H)dione hydrochloride (topotecan hydrochloride) and the process for the synthesis of the same.

BACKGROUND OF THE INVENTION

Topotecan hydrochloride is (10-[(dimethyl amino) methyl]-4-ethyl-4,9-dihydroxy-1H-pyrano[3',4':6,7]indolizino[1,2-b]quinoline-3,14(4H,12H)dione hydrochloride) a compound of formula (I).

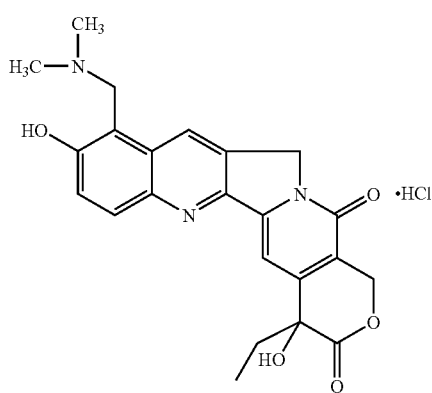

(I)

Topotecan is a semi-synthetic analogue of camptothecin, an agent derived from the Oriental yew tree, Camptothecan accuminata. The cytotoxic effects of the camptothecins are believed to be related to their activity as inhibitors of topoisomerase-I, an enzyme involved in the replication and repair of nuclear DNA. As DNA is replicated in dividing cells, topoisomerase-I acts by binding to super-coiled DNA and causing single-stranded breaks in that DNA. As a result, topoisomerase-I is able to relieve the torsional stresses that are introduced into DNA ahead of the replication complex or moving replication fork. Topotecan inhibits topoisomerase-I by stabilizing the covalent complex of enzyme and strand-cleaved DNA, which is an intermediate of the catalytic mechanism, thereby inducing breaks in the protein-associated DNA single-strands, resulting in cell death. Topotecan hydrochloride stops the growth of cancer cells by preventing the development of elements necessary for cell division.

U.S. Pat. No. 5,004,758 discloses water soluble Camptothecin analogs, which includes topotecan (9-dimethylamino methyl-10-hydroxy camptothecin), preferably (S)-topotecan and its Hydrochloride salt.

U.S. Pat. No. 5,734,056 disclose Camptothecin analogs (which include topotecan) and a process for the preparation of such analogs and its intermediates.

U.S. Pat. No. 5,155,225 describes processes for making Pyrano[3',4':6,7]indolizino-[1,2-B]quinolinones.

WO2005046608 discloses a novel crystalline form of topotecan monohydrochloride pentahydrate, corresponding pharmaceutical compositions, methods of preparation and use for anti-viral and other cancer-related diseases.

The present invention relates to the solid state physical properties of topotecan hydrochloride. These properties can be influenced by controlling the conditions under which topotecan hydrochloride is obtained in solid form. Solid state physical properties include, for example, the flowability of the milled solid. Flowability affects the ease with which the material is handled during processing into a pharmaceutical product.

Another important solid state property of a pharmaceutical compound is its rate of dissolution in aqueous fluid. The rate of dissolution of an active ingredient in a patient's body fluid can have therapeutic consequences since it imposes an upper limit on the rate at which an orally-administered active ingredient can reach the patient's bloodstream.

Topotecan hydrochloride exhibits polymorphism. Polymorphism is the property of some molecules to adopt more than one crystalline form in the solid state. A single molecule can give rise to a variety of crystalline solids having distinct physical properties that can be measured in a laboratory like its thermal behaviour, e.g. melting point and differential scanning calorimetry (DSC) thermogram, dissolution rate, flowability, X-ray diffraction pattern, infrared absorption spectrum and NMR spectrum.

The differences in the physical properties of polymorphs result from the conformation, orientation and intermolecular interactions of adjacent molecules in the crystalline solid. Rate of dissolution of a pharmaceutical compound depends upon its stable crystalline form. The rate of dissolution can have increased effect on the therapeutic efficacy of the administered drug. Hence, this property of the pharmaceutical compound is considered as an important feature in formulating syrups, elixirs and other liquid medicaments. The solid state form of a compound may also affect its behavior on compaction and its storage stability.

Thus, it is clear from the foregoing discussion, it would be desirable to have active pharmaceutical ingredient in a stable crystalline form having improved bulk handling and dissolution properties and this becomes the object of the present invention.

SUMMARY OF THE INVENTION

An object of the present invention is to provide a novel crystalline polymorphic form of topotecan hydrochloride hereinafter referred to as form A.

Another object of the present invention is to provide a process for preparing the novel crystalline polymorphic form A of topotecan hydrochloride from any crystalline form of topotecan Hydrochloride, pentahydrate or amorphous.

Yet another object of the present invention is to provide a process for the preparation of novel crystalline polymorphic form A of topotecan hydrochloride from topotecan base.

The present invention relates to a novel polymorphic form of topotecan hydrochloride which is hereinafter designated as form A.

According to one aspect of the invention there is provided a crystalline form A of topotecan hydrochloride having an XRPD pattern with peaks at 6.08, 6.94, 8.10, 9.96, 10.16, 11.68, 12.28, 13.08, 13.62, 14.32, 15.44, 16.46, 16.56, 17.58, 18.42, 19.32; 20.14, 21.22, 21.88, 22.54, 22.72, 23.38, 24.14, 24.36, 24.78, 25.02, 25.50, 26.42, 26.86, 27.18, 27.44, 28.10, 28.76, 29.42, 29.68 and 30.02°2θ (+0.2°).

According to one aspect of the invention there is provided a crystalline form A of topotecan hydrochloride having characteristic FT-IR peaks at 1743, 1656, 1596, 1560 and 1507 cm$^{-1}$.

According to one aspect of the invention there is provided a crystalline form A of topotecan hydrochloride having an XRPD pattern as shown in FIG. 1.

According to one aspect of the invention there is provided a crystalline form A of topotecan hydrochloride having an FT-IR spectrum as shown in FIG. 2.

In another aspect, there is provided a process of converting topotecan hydrochloride of any crystalline form, anhydrous, pentahydrate, or amorphous form into the novel crystalline topotecan hydrochloride form A.

In a further aspect, there is provided a process for preparation of topotecan hydrochloride form A from topotecan base by dissolving the latter in suitable organic solvent.

The compound of the present invention, topotecan hydrochloride form A can be formulated into a variety of compositions for administration to humans and mammals. Dosage forms include solid dosage forms like tablets, powders, capsules, sachets, troches and lozenges as well as liquid syrups, suspensions and elixirs. The active ingredient (s) and excipients can be formulated into compositions and dosage forms according to methods known in the art.

According to another aspect of the invention, there is provided a process for preparing crystalline form A of topotecan hydrochloride, comprising: suspending topotecan hydrochloride in methanol; stirring at a temperature ranging from 25 to 30° C.; cooling the reaction mass to −10 to 25° C., preferably while stirring it; and recovering the topotecan hydrochloride form A preferably by filtration and drying. The topotecan hydrochloride used to form the topotecan hydrochloride form A may be formed by convention means. It may be crystalline or amorphous. It may be anhydrous or in the form of the pentahydrate.

According to another aspect of the invention, there is provided a process for preparing crystalline form A of topotecan hydrochloride, comprises suspending topotecan base in methanol; adding aqueous HCl and stirring at 25-30° C.; cooling the reaction mass to a temperature ranging from −10 to 25° C., preferably while stirring it; and recovering the topotecan hydrochloride form A preferably by filtration and drying.

The reaction mass is preferably stirred for about one hour while at 25-30° C. The cooling preferably is carried out over about one hour. The filtration is preferably carried out over about 4-6 hours, e.g. 5 hours, while the filtration is preferably carried out over 30 to 40 hours, e.g. 36 hours.

BRIEF DESCRIPTION OF THE DRAWINGS

The invention is illustrated by reference to the accompanying drawings described below.

DETAILED DESCRIPTION OF THE INVENTION

The present invention relates to a novel polymorphic form of topotecan hydrochloride which is hereinafter designated as form A. In one aspect the present invention provides a novel crystalline polymorphic form A of topotecan hydrochloride which is characterized by an XRD pattern (FIG. 1) having peak positions at 6.08, 6.94, 8.10, 9.96, 10.16, 11.68, 12.28, 13.08, 13.62, 14.32, 15.44, 16.46, 16.56, 17.58, 18.42, 19.32; 20.14, 21.22, 21.88, 22.54, 22.72, 23.38, 24.14, 24.36, 24.78, 25.02, 25.50, 26.42, 26.86, 27.18, 27.44, 28.10, 28.76, 29.42, 29.68 and 30.02°2θ (±0.2°).

Figure 2:
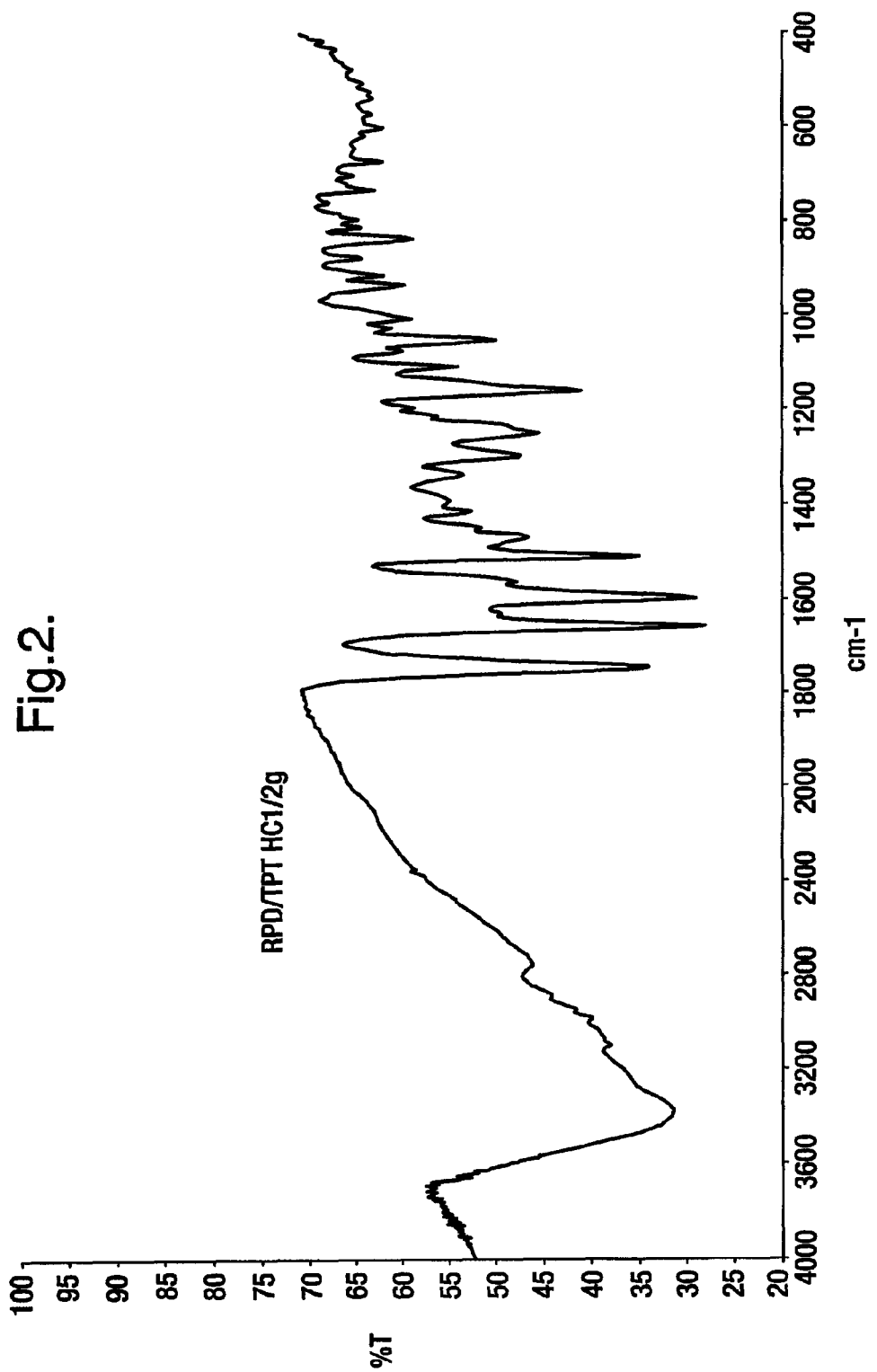
FIG. 2 shows FT-IR (KBr) spectrum of the form A crystalline polymorph of topotecan hydrochloride.

The present invention also provides a novel crystalline polymorphic form A of topotecan hydrochloride characterized by FT-IR (KBr) spectrum as depicted in FIG. 2. Form A provides an infrared spectrum containing peaks at 1743, 1656, 1596, 1560 and 1507.

In another aspect the present invention provides a process of preparing a novel crystalline polymorphic form A of topotecan hydrochloride which comprises suspending topotecan base in a suitable solvent preferably methanol and adding aqueous HCl and stirring at 25-30° C. and further cooling it, preferably while stirring, to at a temperature ranging from −10 to 25° C. preferably at 10-15° C. and filtering the solid, and drying, preferably at 25-30° C. under vacuum to obtain uniform crystals of topotecan hydrochloride form A. The stirring of the reaction mass at 25-30° C. is preferably carried out for about 1 hour.

In another aspect, the present invention provides a process of converting topotecan hydrochloride of any crystalline form, anhydrous, pentahydrate, or amorphous form into the novel crystalline topotecan hydrochloride form A which comprises suspending topotecan hydrochloride in a suitable solvent preferably methanol and stirring at a temperature ranging from −10 to 25° C. preferably at 10-15° C., filtering the solid, and drying at 25-30° C. under vacuum followed by drying, preferably at 30-35° C., for about 36 hours to obtain uniform crystals of topotecan hydrochloride form A.

The topotecan hydrochloride form A of this invention has a water content in the range of 10 to 12%.

The novel crystalline polymorphic form A of topotecan hydrochloride is readily isolated, and displays uniformity, reproducibility, ease and safety of handling in manufacture and stability on isolation and drying.

The topotecan hydrochloride form A is preferably provided in the form of the (4S)-isomer. The purity of the isomer may be up to about 99.5%.

The topotecan hydrochloride according to the invention may be combined with a pharmaceutically acceptable carrier to form suitable pharmaceutical compositions. It may be used in therapy such as in a method of treating tumours.

According to another aspect of the invention, there is provided the crystalline form A of topotecan hydrochloride as described above for use in therapy.

According to another aspect of the invention, there is provided the crystalline form A of topotecan hydrochloride as described above for use in the treatment of a tumour.

According to another aspect of the invention, there is provided the crystalline form A of topotecan hydrochloride as described above for use in the manufacture of a medicament for the treatment of a tumour.

According to another aspect of the invention, there is provided a method of treating a tumour comprising administering a therapeutically effective amount of a crystalline form A of topotecan hydrochloride as described above, to a patient in need thereof. A typical dosage would be about 4 mg, suitably provided in an injection formulation.

EXAMPLES

The nature of the invention, its object and advantages are explained hereunder in greater detail in relation to non-limiting exemplary embodiments.

Example 1

Preparation of Topotecan Hydrochloride (Form A)

10 grams of topotecan hydrochloride amorphous form was suspended in 100 ml of Methanol at 25-30° C. The mixture was stirred for 1 hour at 25-30° C. and further chilled to 10-15° C. and stirred for additional 1 hour at 10-15° C. and filtered; the solid was washed with 5 ml of methanol. The resulting product was dried under vacuum at 25-30° C. for 5 hours, followed by drying at 30-35° C. for 36 hours to give 9.0 g of topotecan hydrochloride form A.

Example 2

Preparation of Topotecan Hydrochloride (Form A)

10.0 g of topotecan hydrochloride pentahydrate was suspended in 100 ml of methanol and stirred at 25-30° C. for 1 hour and further chilled to 10-15° C. and stirred for 1 hour at 15° C. The resulting solid was filtered and washed with 5 ml of methanol. The solid was dried in vacuum at 25-30° C. for 5 hours, followed by drying at 30-35° C. for 36 hours to get 6.0 g of form A.

Example 3

Preparation of Topotecan Hydrochloride (Form A)

10 grams of topotecan base was suspended in 100 ml Methanol, and 2.4 ml HCl was added at 25-30° C. and stirred for 1 hour at 25-30° C., the suspension was further chilled to 10-15° C. and stirred for 1 hour at 10-15° C. and filtered, washed with 5 ml of methanol. The product was dried in vacuum at 25-30° C. for 5 hours, followed by drying at 30-35° C. for 36 hours to get 8.0 g of topotecan hydrochloride form A.

What is claimed as our invention is:

1. A crystalline form A of topotecan hydrochloride having an XRPD pattern with peaks at 6.08, 6.94, 8.10, 9.96, 10.16, 11.68, 12.28, 13.08, 13.62, 14.32, 15.44, 16.46, 16.56, 17.58, 18.42, 19.32; 20.14, 21.22, 21.88, 22.54, 22.72, 23.38, 24.14, 24.36, 24.78, 25.02, 25.50, 26.42, 26.86, 27.18, 27.44, 28.10, 28.76, 29.42, 29.68 and 30.02°2θ (±0.2°).

2. A crystalline form A of topotecan hydrochloride having characteristic FT-IR peaks at 1743, 1656, 1596, 1560 and 1507 cm$^{-1}$.

3. A crystalline form A of topotecan hydrochloride according to claim 1, wherein the Topotecan hydrochloride has a water content in the range of about 10 to 12 wt %.

4. A crystalline form A of topotecan hydrochloride according to claim 2, wherein the Topotecan hydrochloride has a water content in the range of about 10 to 12 wt %.

Figure 1:
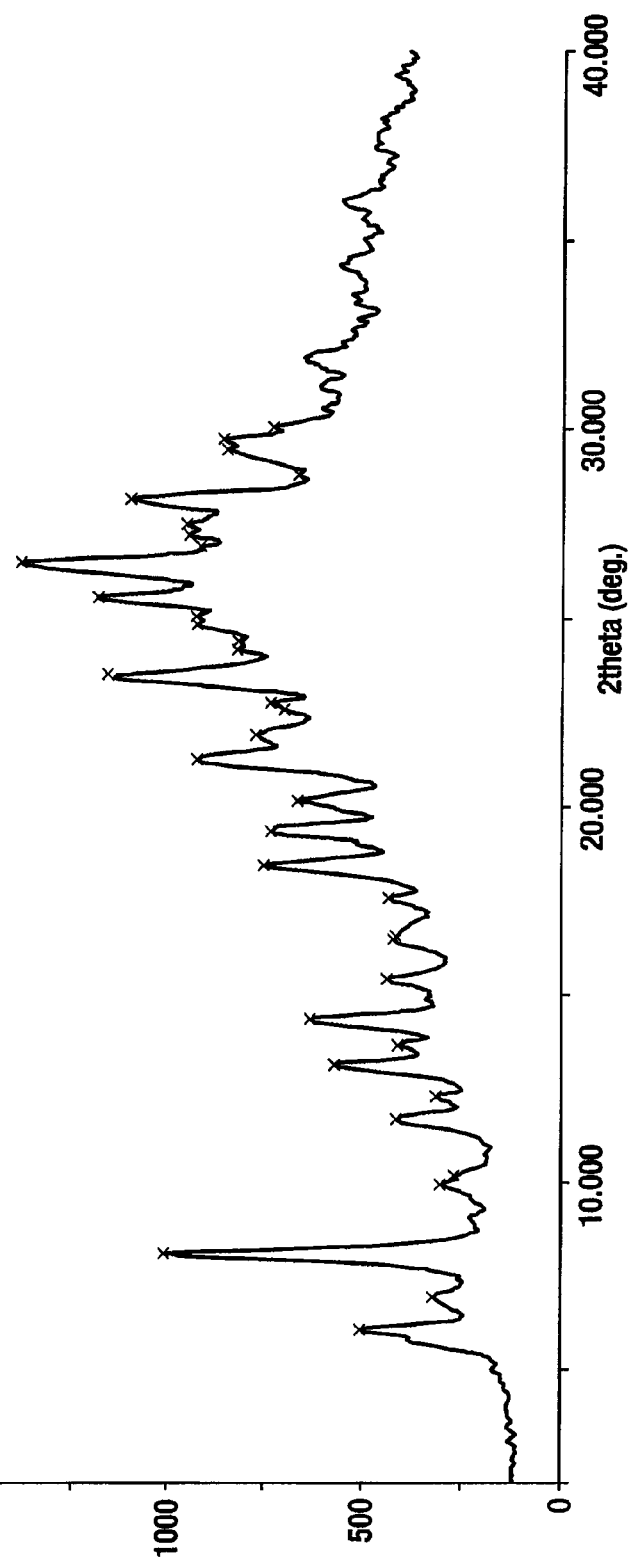
FIG. 1 shows powder X-ray diffractogram of the form A crystalline polymorph of topotecan hydrochloride.

5. A crystalline form A of topotecan hydrochloride having an XRPD pattern as shown in FIG. 1.

6. A crystalline form A of topotecan hydrochloride having an FT-IR spectrum as shown in FIG. 2.

7. A crystalline form A of topotecan hydrochloride having a water content in the range of about 10 to 12 wt %.

8. A crystalline form A of topotecan hydrochloride according to claim 1 comprising (4S)-topotecan hydrochloride.

9. A crystalline form A of topotecan hydrochloride according to claim 2 comprising (4S)-topotecan hydrochloride.

10. A crystalline form A of topotecan hydrochloride according to claim 5 comprising (4S)-topotecan hydrochloride.

11. A crystalline form A of topotecan hydrochloride according to claim 6 comprising (4S)-topotecan hydrochloride.

12. A process for preparing crystalline form A of topotecan hydrochloride, comprising: suspending topotecan hydrochloride in methanol; stirring at a temperature ranging from 25 to 30° C.; cooling the reaction mass to −10 to 25° C.; and recovering the topotecan hydrochloride form A by filtration and drying.

13. A process according to claim 12, wherein the reaction mass is cooled to a temperature ranging from 10 to 15° C.

14. A process according to claim 12, wherein the reaction mass is stirred during said cooling step.

15. A process for preparing crystalline form A of topotecan hydrochloride, comprises suspending topotecan base in methanol; adding aqueous HCl and stirring at 25-30° C.; cooling the reaction mass to a temperature ranging from −10 to 25° C.; and recovering the topotecan hydrochloride form A by filtration and drying.

16. A process according to claim 15, wherein the reaction mass is cooled to a temperature ranging from 10 to 15° C.

17. A process according to claim 15, wherein the reaction mass is stirred during said cooling step.

18. A pharmaceutical formulation comprising a crystalline form A of topotecan hydrochloride of claim 1 in combination with a pharmaceutically acceptable carrier.

19. A method of treating a tumour comprising providing a therapeutically effective amount of a crystalline form A of topotecan hydrochloride of claim 1 to be administered to a patient in need thereof.

* * * * *